United States Patent [19]

Hagiya et al.

[11] Patent Number: 4,962,233
[45] Date of Patent: Oct. 9, 1990

[54] PROCESS FOR PREPARING RACEMIC DIHALOVINYLCYCLOPROPANE CARBOXYLIC ACID HALIDES

[75] Inventors: Koji Hagiya; Gohfu Suzukamo, both of Osaka; Masami Fukao, Shiga; Hiroko Sakane, Osaka, all of Japan

[73] Assignee: Sumitomo Chemical Co., Ltd., Osaka, Japan

[21] Appl. No.: 349,056

[22] Filed: May 9, 1989

[30] Foreign Application Priority Data

| May 19, 1988 | [JP] | Japan | 63-122843 |
| May 26, 1988 | [JP] | Japan | 63-128627 |
| Jul. 13, 1988 | [JP] | Japan | 63-175652 |
| Jul. 13, 1988 | [JP] | Japan | 63-175653 |
| Aug. 9, 1988 | [JP] | Japan | 63-199156 |

[51] Int. Cl.$^5$ .............................................. C07C 61/40
[52] U.S. Cl. ............................ 562/866; 562/867; 560/124
[58] Field of Search ............................ 562/866, 867

[56] References Cited

U.S. PATENT DOCUMENTS

| 3,090,307 | 5/1963 | Illing et al. ............... 260/537 |
| 3,989,750 | 11/1976 | Nagase et al. ............... 260/544 L |
| 4,182,906 | 1/1980 | Suzukamo et al. ............... 562/506 |

FOREIGN PATENT DOCUMENTS 0261824  3/1988  European Pat. Off. .
2352768  1/1978  France .

OTHER PUBLICATIONS

CA(95):97173f, 1981.

Primary Examiner—Paul J. Killos
Attorney, Agent, or Firm—Birch, Stewart, Kolasch & Birch

[57] ABSTRACT

Racemic dihalovinylcyclopropane carboxylic acid halides, which are intermediates of such insecticides as permethrin, cypermethrin etc., are prepared by allowing phosphorus iodides, silicon iodides or boron iodides to react with optically active dihalovinylcyclopropane carboxylic acid halides of the formula:

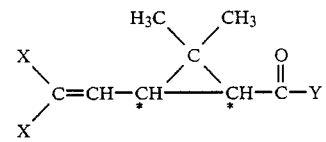

wherein X and Y stand for halogen atoms and the mark * indicates an asymmetric carbon atom.

42 Claims, No Drawings

PROCESS FOR PREPARING RACEMIC DIHALOVINYLCYCLOPROPANE CARBOXYLIC ACID HALIDES

The present invention relates to a process for preparing racemic dihalovinylcyclopropane carboxylic acid halides having the formula

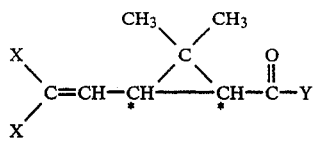

where both X and Y stand for halogen atoms and the mark * indicates an asymmetric carbon atom.

Dihalovinylcyclopropane carboxylic acids, e.g., 2,2-dimethyl-3-(2,2-dihalovinyl)-cyclopropane carboxylic acid (hereinafter referred to as dihalo acid) corresponding to the compound belonging to the formula (I) where Y is a hydroxyl group is an acid moiety of permethrin, cypermethrin etc., insecticides which are familiar as household ones and are strongly active against agricultural or forest pests. Dihalo acid halides are useful as intermediates of these insecticides.

Dihalo acid halides having the formula (I) have four isomers, i.e., two geometrical isomers, cis and trans, each of which has two optical isomers, (+) and (−). It has been known that, in generel, the pyrethroidal esters derived from (+) isomers have greater insecticidal activity than those derived from (−) isomers and that esters in the trans form are far less toxic against mammals than those in the cis form (Nature 244, 456, 1973). Dihalo acids industrially available are usually in the racemic mixture, i.e., as (±) form, each of which is in a mixture of cis- and trans isomers. Optical resolution of the acids by means of an optically active organic base is effected to obtain (+)-isomers which are used for preparing highly active insecticidal compounds. Alternatively, asymmetric hydrolysis with enzymes is also effected to obtain the effective isomers, when the acids above are in the form of esters. Wherein, the remaining (−)-isomer after the resolution is least useful, since the esters composed thereof are almost inactive. Accordingly, it is a problem to be solved in the production of the (+)-form acid, particularly on a commercial scale, that the (+)-form acid be racemized with a high efficiency, so as to be utilized again as the material for the optical resolution method above. However, a great difficulty is encountered in the racemization, since the cyclopropane carboxylic acids of the formula (I) above have two asymmetric carbon atoms at $C_1$ and $C_3$.

A method for racemization of dihalo acids is reported in which the reaction is conducted by irradiating the dihalo acids with ultraviolet rays in the presence of photosensitizers (Japanese Patent Kokai 50-160242). However, the process is not necessarily economical, since an expensive apparatus for the photochemical reaction and a large amount of electric energy are needed.

After an extensive study, the present inventors succeeded in finding the fact that phosphorus iodides, silicon iodides or boron iodides facilitate racemization of optically active dihalo acid halides, and established the present invention after more additional research was conducted.

According to the present invention, a 'process for preparing racemic dihalovinylcyclopropane carboxylic acid halides by allowing iodides selected from phosphorus iodides, silicon iodides and boron iodides to react with optically active dihalovinylcyclopropane carboxylic acid halides of the formula

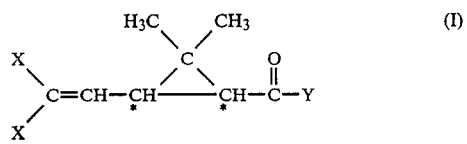

wherein both X and Y are halogen atoms and the mark * indicates asymmetric carbon atoms.

Optically active dihalo acid halides (I) include, for example, optically active dichloro acid chloride, difluoro acid chloride, chlorofluoro acid chloride, dibromo acid chloride, dichloro acid bromide or dibromo acid bromide, usually dihalo acid chlorides are preferable from the point of convenience in handling and cost.

There are four isomers as stated above in the dihalo acid halides. Any of the four isomers can be used as starting material, either alone or in mixtures. The racemization can be attained irrespective of the optical purity of the starting material. The racemization method always gives the trans-rich reaction product regardless of the isomeric composition of the starting material.

Iodides of phosphorus, silicon or boron are, for example, phosphorus triiodide, silicon tetraiodide or boron triiodide. They are used usually in an amount of 1/200–1, preferably 1/100–1/10 times as much as dihalo acid halides, in moles.

The use of iodine halides together with phosphorus iodides or the use of iodine together with silicon iodides facilitates the racemization reaction. An amount of the iodine halides or- iodine is usually 1/200–1, preferably 1/100–1/10 times as much as dihalo acid halides, in mole. Iodine halides are, for example, iodine, iodine bromide or iodine chloride.

The racemization is usually conducted in the presence of inert organic solvents. They are, for example, aromatic hydrocarbons such as benzene, toluene, xylene, cumene, trimethylbenzene or nitrobenzene; halogenated hydrocarbons such as chloroform, carbon tetrachloride, chlorobenzene, o-dichlorobenzene or bromobenzene; saturated hydrocarbons such as hexane, heptane, cyclohexane or cycloheptane; ethers such as tetrahydropyran, 1,4-dioxane, 1,3-dioxane, tetrahydrofuran, 2-methyltetrahydrofuran, isopropyl ether, dibutyl ether or butyl methyl ether; or nitriles such as acetonitrile, propionitrile or butyronitrile, preferably halogenated hydrocarbons.

The racemization is usually conducted in such a manner that phosphorus iodides, silicon iodides or boron iodides and then, if desired, iodine halides are added to a solution of dihalo acid halides in the solvents Reaction temperature is usually 40°–150° C., preferably 80°–120° C., although it varies depending on amounts and kinds of phosphorus iodides, silicon iodides or boron iodides employed.

Reaction time is usually from 30 min to 20 hours, although it varies depending on amounts and kinds of phosphorus iodides, silicon iodides, boron iodides and iodine halides.

Progress of the reaction may be checked by analysing a portion of reaction mixture with gas chromatography or NMR or IR spectroscopy To the reaction mass or the reaction product which has been isolated from the reaction mixture are added 2-phenoxybenzyl alcohol, 5-benzyl-3-furylmethyl alcohol, 4-methyl-3-heptene-6-in-5-ol or 4-fluoro-3-heptene-6-in-5-ol to prepare low mammalian toxic insecticides. The isolation of the product compound is effected in such a manner that the reaction mass from which a catalyst has been removed is subjected to distillation or the like. Alternatively, ethanol or the like is added to the reaction mass to effect direct esterification and then the product may be subjected to biochemically optical resolution. Another approach is addition of aqueous alkaline solution to the reaction mass until free acids are obtained by hydrolysis.

According to the present process, racemic dihalo acids are produced with high efficiency without specific apparatuses. The racemic dihalo acids obtained are rich in trans-isomers which are low-toxic against mammals.

The present process can also be used for conversion of racemic cis-isomer or racemic mixture of cis- and trans-isomers of dihalo acid halides into the corresponding racemic trans-rich isomer.

The present invention is explained in more detail by examples

EXAMPLE 1

To a solution of levo-rotatory dichloro acid chloride (1.03 g; composition: (+)-cis 18.6%, (−)-cis 78.0%, (+)-trans 1.6%, and (−)-trans 1.8%) in chlorobenzene (22 g) were added phosphorus triiodide (300 mg) and iodine (50 mg) under a nitrogen atmosphere. The mixture was stirred at 100° C. for 10 hours.

Then, a part of the reaction solution was taken as a sample and converted to ester with (+)-2-octanol. Gas chromatographic analysis gave the following optical isomer ratio: (+)-cis 10%, (−)-cis 14.6%, (+)-trans 39.4% and (−)-trans 36.0%.

The reaction solution was cooled to room temperature, and thereto were added ethanol (230 mg) and pyridine (390 mg). The mixture was stirred at room temperature for 1 hour, washed with water and subjected to distillation to remove the solvent. Solution thus obtained was distilled off to obtain a fraction (960 mg, a boiling point: 88°–90° C./1 mmHg). This product was identified as dichloro acid ethyl ester by IR spectrum.

EXAMPLE 2

To a solution of levo-rotatory dichloro acid chloride (1.95 g; composition: (+)-trans 7.1% and (−)-trans 92.9%) in chlorobenzene (24 g) were added phosphorus triiodide (150 mg) and iodine (92 mg) under a nitrogen atmosphere. The mixture was stirred at 100° C. for 13 hours.

Then, the similar procedure to that in Example 1 was applied to until dichloro acid ethyl ester (1.91 g) was obtained. The optical isomer ratio: (+)-cis 9.9%, (−)-cis 8.5%, (+)-trans 34.4% and (−)-trans 47.2%.

EXAMPLE 3

To a solution of the same dichloro acid chloride (3.24 g) as used in Example 1 in chlorobenzene (47 g) were added phosphorus triiodide (750 mg) and iodine-monochloride (150 mg) under a nitrogen atmosphere. The mixture was stirred at 100° C. for 6 hours.

Then, the mixture was cooled to room temperature, hydrolyzed with 15% aqueous sodium hydroxide solution, acidified with 70% sulfuric acid and extracted with toluene. The toluene was removed by distillation to obtain a white solid (2.67 g). The solid was identified as dichloro acid by IR spectrum A part of the solid was taken as a sample and converted to (+)-2-octyl ester by a usual manner. Gas chromatographic analysis gave the following optical isomer ratio (+)-cis 7.9%, (−)-cis 11.5%, (+)-trans 41.6% and (−)-trans 39.0%.

EXAMPLE 4

To a solution of the same dichloro acid chloride (1.05 g) as used in Example 1 in chlorobenzene (16 g) were added phosphorus triiodide (260 mg) and iodine monobromide (140 mg) under a nitrogen atmosphere The mixture was stirred at 100° C. for 4 hours.

Then, the similar procedure to that in Example 1 was applied to until dichloro acid ethyl ester (1.03 g) was obtained.

The optical isomer ratio: (+)-cis 8.6%, (−)-cis 11.6%, (+)-trans 41.8% and (−)-trans 38.0%.

EXAMPLE 5

To a solution of the same dichloro acid chloride (930 mg) as used in Example 1 in 1,4-dioxane (20 g) were added phosphorus triiodide (310 mg) and iodine (190 mg) under a nitrogen atmosphere. The mixture was stirred at 100° C. for 4 hours.

Then, the similar procedure to that in Example 1 was applied to until dichloro acid ethyl ester (856 mg) was obtained.

The optical isomer ratio: (+)-cis 7.3%, (−)-cis 10.8%, (+)-trans 45.7% and (−)-trans 36.2%.

EXAMPLE 6

To a solution of the same dichloro acid chloride (980 mg) as used in Example 2 in 1,2-dichloroethane (23 g) were added phosphorus triiodide (550 mg) and iodine (170 mg) under a nitrogen atmosphere. The mixture was stirred at 80° C. for 14 hours.

The optical isomer ratio: (+)-cis 7.9%, (−)-cis 8.0%, (+)-trans 38.7% and (−)-trans 45.4%.

EXAMPLE 7

To a solution of levo-rotatory dichloro acid chloride (2.5 g; composition: (+)-cis 4.1%, (−)-cis 2.9%, (+)-trans 13.8% and (−)-trans 79.2%) in chlorobenzene (18 g) were added silicon tetraiodide (590 mg) and iodine (140 mg) under a nitrogen atmosphere. The mixture was stirred at 100° C. for 4 hours.

A part of the reaction solution was converted to ester with (+)-2-octanol. Gas chromatographic analysis gave the following optical isomer ratio: (+)-cis 9.4%, (−)-cis 7.8%, (+)-trans 34.7% and (−)-trans 48.1%.

The reaction solution was cooled to room temperature and thereto were added ethanol (660 mg) and pyridine (1.13 g). The mixture was stirred at room temperature for 1 hour and washed with water. After the solvent was evaporated, the residue was distilled to give a fraction (2.37 g, a boiling point: 88–90° C./1 mmHg). The fraction was identified as dichloro acid ethyl ester by IR spectrum.

EXAMPLE 8

To a solution of the same dichloro acid chloride (2.5 g) as used in Example 7 in chlorobenzene (11 g) were added silicon tetraiodide (625 mg) and iodine (100 mg) under a nitrogen atmosphere. The mixture was stirred at 110° C. for 6 hours.

Then, the reaction mixture was worked up according to the treatment in Example 7 to give dichloro acid ethyl ester (2.18 g).

The optical isomer ratio: (+)-cis 9.3%, (−)-cis 8.2%, (+)-trans 36.3% and (−)-trans 46.2%.

EXAMPLE 9

To a solution of the same dichloro acid chloride (2.5 g) as used in Example 7 in toluene (14 g) were added silicon tetraiodide (1.08 g) and iodine (274 mg) under a nitrogen atmosphere. The mixture was stirred at 100° C. for 8 hours.

The optical isomer ratio: (+)-cis 8.1%, (−)-cis 7.3%, (+)-trans 37.7% and (−)-trans 46.9%.

EXAMPLE 10

To a solution of the same dichloro acid chloride (1.01 g) as used in Example 2 in chlorobenzene (23 g) was added phosphorus triiodide (630 mg) under a nitrogen atmosphere. The mixture was stirred at 100° C. for 9 hours. The reaction mixture was worked up according to the treatment in Example 1 to give dichloro acid ethyl ester.

The optical isomer ratio: (+)-cis 8.9%, (−)cis 8.6%, (+)-trans 37.5% and (−)-trans 45.0%.

EXAMPLE 11

To a solution of the same dichloro acid chloride (2.5 g) as used in Example 7 in chlorobenzene (14 g) was added silicon tetraiodide (567 mg) under a nitrogen atmosphere. The mixture was stirred at 100° C. for 4 hours.

The reaction mixture was worked up according to the treatment in Example 7 to give dichloro acid ethyl ester (2.17 g).

The optical isomer ratio: (+)-cis 11.3%, (−)-cis 5.7%, (+)-trans 25.3% and (−)-trans 57.7%.

EXAMPLE 12

To a solution of the same dichloro acid chloride (2.5 g) as used in Example 7 in acetonitrile (31 g) was added silicon tetraiodide (1.17 g) under a nitrogen atmosphere. The mixture was stirred at 80° C. for 8 hours.

The reaction mixture was worked up according to the treatment in Example 7 to give dichloro acid ethyl ester.

The optical isomer ratio: (+)-cis 8.6%, (−)-cis 4.8%, (+)-trans 27.9% and (−)-trans 58.7%.

EXAMPLE 13

To a solution of levo-rotatory dichloro acid chloride (1.21 g; composition: (+)-cis 3.0%, (−)-cis 2.9%, (+)-trans 14.1% and (−)-trans 80.0%) in chlorobenzene (22 g) was added boron triiodide (290 mg) under a nitrogen atmosphere. The mixture was stirred at 100° C. for 8 hours.

A part of the reaction solution was converted to ester with (+)-2-octanol. Gas chromatographic analysis gave the optical isomer ratio: (+)-cis 11.4%, (−)-cis 7.2%, (+)-trans 28.6% and (−)-trans 52.8%.

The reaction mixture was cooled to room temperature, and ethanol (270 mg) and pyridine (460 mg) were added thereto. The mixture was stirred at room temperature for 1 hour and washed with water. After the solvent was evaporated under reduced pressure, the residue was distilled to give a fraction (1.13 g, a boiling point: 88°–90° C./1 mmHg). The fraction was identified as dichloro acid ethyl ester by IR spectrum.

EXAMPLE 14

Example 13 was repeated except that boron triiodide (540 mg) and chlorobenzene (6 g) were used to obtain dichloro acid ethyl ester (1.07 g).

The optical isomer ratio: (+)-cis 9.9%, (−)-cis 7.6%, (+)-trans 38.2% and (−)-trans 44.3%.

EXAMPLE 15

To a solution of the same levo-rotatory dichloro acid chloride (1.21 g) as used in Example 1 in 1,2-dichloroethane (25 g) was added boron triiodide (320 mg) under a nitrogen atmosphere. The mixture was stirred at 80° C. for 8 hours.

Then, the reaction mixture was cooled to room temperature. The reaction mixture was hydrolyzed with 15% aqueous sodium hydroxide solution, acidified with 70% sulfuric acid and extracted with toluene. The toluene was removed by distillation to obtain a white solid (1 g). The solid was identified as dichloro acid by IR spectrum. A portion of the solid was converted to (+)-2-octyl octyl ester by a usual manner. Gas chromatographic analysis gave the following optical isomer ratio: (+)-cis 6.4%, (−)-cis 12.2%, (+)-trans 54.1% and (−)-trans 27.3%.

EXAMPLE 16

To a solution of the same dichloro acid chloride (1.19 g) as used in Example 1 in toluene (17.4 g) was added boron triiodide (320 mg) under a nitrogen atmosphere The mixture was stirred at 100° C. for 8 hours.

Then, the reaction mixture was worked up according to the treatment in Example 13 to give dichloro acid ethyl ester (1.09 g). The optical isomer ratio: (+)-cis 7.6%, (−)-cis 21.1%, (+)-trans 50.9% and (−)-trans 20.4%.

EXAMPLE 17

To a solution of the same dichloro acid chloride (1.35 g) as used in Example 1 in acetonitrile (15.7 g) was added boron triiodide (390 mg) under a nitrogen atmosphere. The mixture was stirred at 80° C. for 10 hours.

Then, the reaction mixture was worked up according to the treatment in Example 13 to give dichloro acid ethyl ester (1.16 g). The optical isomer ratio: (+)-cis 5.2%, (−)-cis 9.6%, (+)-trans 57.4% and (−)-trans 27.8%.

COMPARATIVE EXAMPLE 1

Example 13 was repeated except that boron tribromide (190 mg) was used in place of boron triiodide.

The optical isomer ratio (+)-cis 3.9%, (−)-cis 3.7%, (+)-trans 15.7% and (−)-trans 76.7%.

COMPARATIVE EXAMPLE 2

Example 13 was repeated except that boron trichloride (190 mg) was used in place of boron triiodide.

The optical isomer ratio: (+)-cis 3.0%, (−)-cis 3.0%, (+)-trans 14.0% and (−)-trans 80.0%.

EXAMPLE 18

To a solution of dichloro acid chloride (1.95 g; composition: cis 96.3% and trans 3.7%) in chlorobenzene (20 g) were added phosphorus triiodide (260 mg) and iodine (160 mg) under a nitrogen atmosphere. The mixture was stirred at 80° C. for 6 hours.

Then, the reaction mixture was cooled to room temperature. Ethanol (430 mg) and pyridine (750 mg) were added to the solution The mixture was stirred at room temperature for one hour and washed with water. After the solvent was removed by distillation, the remaining solution was subjected to distillation to obtain a fraction (1.89 g, a boiling point: 88°-90° C./1 mmHg). The fraction was identified as dichloro acid ethyl ester by IR spectrum Gas chromatographic analysis gave the following result: cis 21.1% and trans 78.9%.

EXAMPLE 19

To a solution of dichloro acid chloride (3.24 g; composition: cis 96.6% and trans 3.4%) in chlorobenzene (47 g) were added phosphorus triiodide (750 mg) and iodinemonochloride (150 mg) under a nitrogen atmosphere. The mixture was stirred at 100° C. for 6 hours.

Then, the reaction mixture was cooled to room temperature, hydrolyzed with 15% aqueous sodium hydroxide solution, acidified with 70% sulfuric acid and extracted with toluene. The toluene was removed by distillation to obtain a white solid (2.67 g). The solid was identified as dichloro acid by IR spectrum.

A portion of the solid was converted to ethyl ester by a usual manner. Gas chromatographic analysis gave the following result: cis 19.4% and trans 80.6%.

EXAMPLE 20

To a solution of the same dichloro acid chloride (1.05 g) as used in Example 19 in chlorobenzene (16 g) were added phosphorus triiodide (260 mg) and iodine monobromide (140 mg) under a nitrogen atmosphere. The mixture was stirred at 100° C. for 4 hours.

Then, the reaction mixture was worked up according to the treatment in Example 18 to give dichloro acid ethyl ester (1.03 g).

Gas chromatographic analysis gave the following isomer ratio: cis 20.2% and trans 79.8%.

EXAMPLE 21

To a solution of the same dichloro acid chloride (2.34 g) as used in Example 18 in chlorobenzene (24 g) were added phosphorus triiodide (330 mg) and iodine (200 mg) under a nitrogen atmosphere. The mixture was stirred at 65° C. for 10 hours.

Then, the reaction mixture was worked up according to the treatment in Example 18. Gas chromatographic analysis gave the following isomer ratio: cis 39% and trans 61%.

EXAMPLE 22

To a solution of the same dichloro acid chloride (1.37 g) as used in Example 18 in 1,2-dichloroethane (26 g) were added phosphorus triiodide (170 mg) and iodine (100 mg) under a nitrogen atmosphere. The mixture was stirred at 80° C. for 6 hours.

Then, the reaction mixture was worked up according to the treatment in Example 18 to give dichloro acid ethyl ester (1.30 g). Gas chromatographic analysis gave the following isomer ratio: cis 25.7% and trans 74.3%.

EXAMPLE 23

To a solution of the same dichloro acid chloride (930 mg) as used in Example 19 in 1,4-dioxane (20 g) were added phosphorus triiodide (310 mg) and iodine (190 mg) under a nitrogen atmosphere. The mixture was stirred at 100° C. for 4 hours.

Then, the reaction mixture was worked up according to the treatment in Example 18 to give dichloro acid ethyl ester (856 mg). Gas chromatographic analysis gave the following isomer ratio: cis 18.1% and trans 81.9%.

EXAMPLE 24

To a solution of the same dichloro acid chloride (2 g) as used in Example 18 in chlorobenzene (7.5 g) were added silicon tetraiodide (207 mg) and iodine (105 mg) under a nitrogen atmosphere The mixture was stirred at 80° C. for 4 hours.

Then, the reaction solution was cooled to room temperature. Ethanol (526 mg) and pyridine (903 mg) were added to the solution. The mixture was stirred at room temperature for 1 hour and washed with water. After the solvent was removed by distillation, the residue was subjected to distillation to obtain a fraction (1.96 g, a boiling point: 88°-90° C./1 mmHg). The fraction was identified as dichloro acid ethyl ester by IR spectrum.

Gas chromatographic analysis gave the following isomer ratio: cis 17.1% and trans 82.9%.

EXAMPLE 25

To a solution of the same dichloro acid chloride (2 g) as used in Example 18 in chlorobenzene (18 g) were added silicon tetraiodide (217 mg) and iodine monochloride (61 mg) under a nitrogen atmosphere. The mixture was stirred at 80° C. for 4 hours.

Then, the reaction mixture was worked up according to the treatment in Example 24 to give dichloro acid ethyl ester (1.95 g).

Isomer ratio was as follows: cis 17.3% and trans 82.7%

EXAMPLE 26

To a solution of the same dichloro acid chloride (2 g) as used in Example 18 in chlorobenzene (18 g) were added silicon tetraiodide (212 mg) and iodine-monobromide (122 mg) under a nitrogen atmosphere. The mixture was stirred at 80° C. for 4 hours.

Then, the reaction mixture was worked up according to the treatment in Example 24 to give dichloro acid ethyl ester (1.86 g).

Isomer ratio was as follows: cis 17.3% and trans 82.7%

EXAMPLE 27

To a solution of the same dichloro acid chloride (2 g) as used in Example 18 in acetonitrile (18 g) were added silicon tetraiodide (448 mg) and iodine (212 mg) under a nitrogen atmosphere. The mixture was stirred at 80° C. for 4 hours.

Isomer ratio was as follows: cis 18% and trans 82%.

EXAMPLE 28

To a solution of the same dichloro acid chloride (2 g) as used in Example 18 in dichloroethane (18 g) were added silicon tetraiodide (212 mg) and iodine(100 mg) under a nitrogen atmosphere. The mixture was stirred at 80° C. for 4 hours.

Then, the reaction mixture was worked up according to the treatment in Example 24 to give dichloro acid ethyl ester (1.95 g).

Isomer ratio was as follows: cis 16.8% and trans 83.2%.

EXAMPLE 29

To a solution of the same dichloro acid chloride (1.47 g) as used in Example 18 in chlorobenzene (23 g) was added phosphorus triiodide (140 mg) under a nitrogen atmosphere. The mixture was stirred at 100° C. for 8 hours.

Then, the reaction mixture was worked up according to the treatment in Example 18 to give dichloro acid ethyl ester (1.44 g).

Isomer ratio was as follows: cis 45.5% and trans 54.5%.

EXAMPLE 30

To a solution of the same dichloro acid chloride (2 g) as used in Example 18 in chlorobenzene (8.1 g) was added silicon tetraiodide (198 mg) under a nitrogen atmosphere. The mixture was stirred at 80° C. for 4 hours Then, the reaction mixture was worked up according to the treatment in Example 18 to give dichloro acid ethyl ester (2.01 g).

Isomer ratio was as follows: cis 27.9% and trans 72.1%.

EXAMPLE 31

To a solution of the same dichloro acid chloride (2.0 g) as used in Example 18 in chlorobenzene (18 g) was added boron triiodide (110 mg) under a nitrogen atmosphere. The mixture was stirred at 100° C. for 3 hours.

Then, the reaction solution was cooled to room temperature. Ethanol (440 mg) and pyridine (770 mg) were added to the solution. The mixture was stirred at room temperature for 1 hour and washed with water. After the solvent was distilled, the residue solution was subjected to distillation to obtain a fraction (2.0 g, a boiling point 88°-90° C./1 mmHg).

The fraction was identified as dichloro acid ethyl ester by IR spectrum. Gas chromatographic analysis gave the following result: cis 21.1% and trans 78.9%.

EXAMPLE 32

To a solution of dichloro acid chloride (3.08 g; composition: cis 45.0% and trans 55.0%) in chlorobenzene (24 g) was added boron triiodide (440 mg) under a nitrogen atmosphere. The mixture was stirred at 80° C. for 6 hours.

Then, the reaction solution was cooled to room temperature, hydrolyzed with 15% aqueous sodium hydroxide solution, acidified with 70% sulfuric acid and extracted with toluene. The toluene was removed by distillation to obtain a white solid (2.64 g). The solid was identified as dichloro acid by IR spectrum.

A portion of the solid was converted to ethyl ester by a usual manner. Gas chromatographic analysis gave the following isomer ratio: cis 20.7% and trans 79.3%.

EXAMPLE 33

To a solution of the same dichloro acid chloride (1.19 g) as used in Example 19 in toluene (17.4 g) was added boron triiodide (320 mg) under a nitrogen atmosphere. The mixture was stirred at 100° C. for 8 hours.

Then, the reaction mixture was worked up according to the treatment in Example 31 to give dichloro acid ethyl ester (1.93 g).

Gas chromatographic analysis gave the following isomer ratio: cis 29.7% and trans 70.3%.

EXAMPLE 34

To a solution of the same dichloro acid chloride (1.21 g) as used in Example 19 in 1,2-dichloroethane (25 g) was added boron triiodide (320 mg) under a nitrogen atmosphere. The mixture was stirred at 80° C. for 4 hours.

Then, the reaction mixture was worked up according to the treatment in Example 31 to give dichloro acid ethyl ester (1.13 g).

Isomer ratio was as follows: cis 18.1% and trans 81.9%.

EXAMPLE 35

To a solution of the same dichloro acid chloride (2.21 g) as used in Example 18 in acetonitrile (26 g) was added boron triiodide (220 mg) under a nitrogen atmosphere. The mixture was stirred at 50° C. for 9 hours.

Then, the reaction mixture was worked up according to the treatment in Example 31. Isomer ratio was as follows: cis 48% and trans 52%.

COMPARATIVE EXAMPLE 3

A solution of the same dichloro acid chloride (1.05 g) as used in Example 18 in chlorobenzene (16 g) was stirred under a nitrogen atmosphere at 100° C. for 8 hours.

Isomer ratio was as follows: cis 94.7% and trans 5.3%.

COMPARATIVE EXAMPLE 4

Example 31 was repeated except that boron tribromide (70 mg) was used in place of boron triiodide.

Gas chromatographic analysis gave the following isomer ratio: cis 95.1% and trans 4.9%.

COMPARATIVE EXAMPLE 5

Example 31 was repeated except that boron trichloride (33 mg) was used in place of boron triiodide.

Gas chromatographic analysis gave the following isomer ratio: cis 96.3% and trans 3.7%.

What is claimed is:

1. A process for preparing racemic dihalovinylcyclopropane carboxylic acid halides which comprises allowing iodides selected from the group consisting of phosphorus iodides, silicon iodides and boron iodides to react with an optionally active 2,2-dimethyl-3-(2,2-dihalovinyl)-cyclopropane carboxylic acid halide of the formula:

$$\underset{X}{\overset{X}{\diagdown}}C=CH-\underset{*}{CH}\underset{\diagup\diagdown}{\overset{H_3C\diagup CH_3}{\underset{C}{\diagup\diagdown}}}\underset{*}{CH}-\overset{O}{\underset{\parallel}{C}}-Y$$

wherein both X and Y are halogen atoms and the mark * indicates an asymmetric carbon atom.

2. A process according to claim 1 wherein the amount of the iodides is from 1/200 to 1 times as much as the amount of the optically active halide to be treated, in moles.

3. A process according to claim 1 wherein the iodides are phosphorous iodides.

4. A process according to claim 1 wherein the phosphorous iodides are phosphorus triiodide.

5. A process according to claim 3 wherein the reaction is conducted in the presence of iodine halides.

6. A process according to claim 5 wherein the iodine halides are iodine, iodine-bromide or iodine-chloride.

7. A process according to claim 5 wherein the amount of the iodine halides is from 1/200 to 1 times as much as the amount of optically active halide to be treated, in moles.

8. A process according to claim 1 wherein the iodides are silicon iodides.

9. A process according to claim 8 wherein the silicon iodides are silicon tetraiodide.

10. A process according to claim 8 wherein the reaction is conducted in the presence of iodine.

11. A process according to claim 10 wherein the amount of the iodine is from 1/200 to 1 times as such as the amount of optically active halide to be treated, in moles.

12. A process according to claim 1 wherein the iodides are boron iodide.

13. A process according to claim 12 wherein the boron iodide is boron triiodide.

14. A process according to claim 1 wherein the reaction is carried out in solvents selected from the group consisting of aromatic hydrocarbons, halogenated hydrocarbons, saturated hydrocarbons, ethers, nitriles and mixtures thereof.

15. A process according to claim 1 wherein the reaction is conducted at a temperature of from 40° to 150° C.

16. A process for preparing trans-2,2-dimethyl-3-(2,2-dihalovinyl)cyclopropane carboxylic acid halides which comprises allowing iodides selected from the group consisting of phosphorus iodides, silicon iodides and boron iodides to react with a cis- or cis-/trans-mixed 2,2-dimethyl-3-(2,2-dihalovinyl)cyclopropane carboxylic acid halide of the formula:

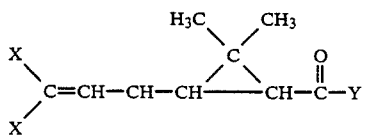

wherein both X and Y are halogen atoms.

17. A process according to claim 16 wherein the amounts of iodides is from 1/200 to 1 times as much as the amount of the cis- or cis-/trans-mixed halide to be treated, in moles.

18. A process according to claim 16 wherein the iodides are phosphorus iodides.

19. A process according to claim 18 wherein the phosphorous iodides are phosphorus triiodide.

20. A process according to claim 18 wherein the reaction is carried out in the presence of iodine halides.

21. A process according to claim 20 wherein the iodine halides are iodine, iodine-bromide or iodine-chloride.

22. A process according to claim 20 wherein the amount of the iodine halides is from 1/200 to 1 times as much as the amount of the cis- or cis-/trans-mixed halide to be treated, in moles.

23. A process according to claim 16 wherein the iodides are silicon iodides.

24. A process according to claim 23 wherein the silicon iodides are silicon tetraiodide.

25. A process according to claim 23 wherein the reaction is conducted in the presence of iodine.

26. A process according to claim 25 wherein the amount of the iodine is from 1/200 to 1 times as much as the amount of the cis- or cis-/trans-mixed halide to be treated, in moles.

27. A process according to claim 16 wherein the iodides are boron iodides.

28. A process according to claim 27 wherein the boron iodides are boron triiodide.

29. A process according to claim 16 wherein the reaction is carried out in solvents selected from the group consisting of aromatic hydrocarbons, halogenated hydrocarbons, saturated hydrocarbons, ethers, nitriles and mixtures thereof.

30. A process according to claim 16 wherein the reaction is conducted at a temperature of from 40° to 150° C.

31. A process according to claim 1 wherein the amount of the iodides is from 1/100 to 1/10 times as much as the amount of the optically active halide to be treated, in moles.

32. A process according to claim 16 wherein the amount of the iodides is from 1/100 to 1/10 times as much as the amount of the cis- or cis-/trans-mixed halide to be treated, in moles.

33. A process according to claim 5 wherein the amount of the iodine halides is from 1/100 to 1/10 times as much as the amount of optically active halide to be treated, in moles.

34. A process according to claim 10 wherein the amount of the iodine is from 1/100 to 1/10 times as much as the amount of the optically active halide to be treated, in moles.

35. A process according to claim 1 wherein the reaction is conducted at a temperature of from 80° to 120° C.

36. A process according to claim 16 wherein the reaction is conducted at a temperature of from 80° to 120° C.

37. A process according to claim 1, which further comprises adding to the racemic dihalovinylcyclopropane carboxylic acid halides prepared according to claim 1 an alcohol selected from the group consisting of 2-phenoxybenzyl alcohol, 5-benzyl-3-furylmethyl alcohol, 4-methyl-3-heptene-6-in-5-ol, and 4-fluoro-3-heptene-6-in-5-ol to prepare insecticides exhibiting low toxicity to mammals.

38. A process according to claim 16, which further comprises adding to the trans-2,2-dimethyl-3-(2,2-dihalovinyl)-cyclopropane carboxylic acid halides prepared according to claim 16 an alcohol selected from the group consisting of 2-phenoxybenzyl alcohol, 5-benzyl-3-furylmethyl alcohol, 4-methyl-3-heptene-6-in-5-ol, and 4-fluoro-3-heptene-6-in-5-ol to prepare insecticides exhibiting low toxicity to mammals.

39. A process according to claim 1 wherein Y is a chlorine atom.

40. A process according to claim 1 wherein Y is a bromine atom.

41. A process according to claim 16 wherein Y is a chlorine atom.

42. A process according to claim 16 wherein Y is a bromine atom.

* * * * *